United States Patent [19]

Purcell et al.

[11] 4,342,759
[45] Aug. 3, 1982

[54] ANTITHROMBOTIC METHOD

[75] Inventors: Thomas A. Purcell, Fontenay aux Roses; Braham Shroot, Sophia Antipolis; Daniel Galtier, St Cyr L'Ecole, all of France

[73] Assignee: Synthelabo, Paris, France

[21] Appl. No.: 179,460

[22] Filed: Aug. 19, 1980

[51] Int. Cl.³ .................... A61K 31/54; A61K 31/495
[52] U.S. Cl. ................................ 424/246; 424/248.4; 424/248.5; 424/248.58; 424/250
[58] Field of Search ............ 424/250, 246, 247, 248.4, 424/248.5, 248.58

[56] References Cited

U.S. PATENT DOCUMENTS 4,243,665  1/1981  Purcell et al. .................... 424/246

Primary Examiner—Anna P. Fagelson
Attorney, Agent, or Firm—Wegner & Bretschneider

[57] ABSTRACT

A method of treating a patient susceptible to thrombosis is provided which comprises treating the said patient with a compound of the formula

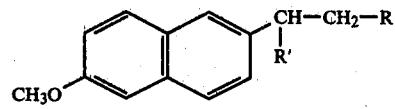

wherein
R' is H or CH₃
R is a

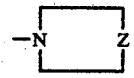

radical in which Z is O, S, SO, SO$_2$ or NR$_1$, R$_1$ being H, C$_6$H$_5$, CH$_3$, CONR$_2$R$_3$, COOR$_2$, COR$_2$ or SO$_2$R$_2$, where R$_2$ and R$_3$ are, independently, H, C$_{1-4}$ alkyl, C$_6$H$_5$ or CF$_3$.

2 Claims, No Drawings

ANTITHROMBOTIC METHOD

The compounds may be in the form of a racemate or its énantiomers or in the form of a pharmaceutically acceptable salt.

The compounds of the invention are prepared in accordance with the method of U.S. patent application Ser. No. 962,760 of Nov. 21, 1978, now U.S. Pat. No. 4,243,665, granted Jan. 6, 1981.

The following example illustrates the preparation.

EXAMPLE

2-[2-(4-isopropylaminocarbonylpiperazino)-1-methylethyl]-6-methoxynaphthalene or its hydrochloride

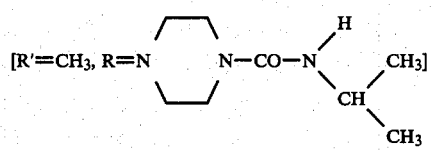

15.82 g (0.056 mol) of 2-(2-piperazino-1-methylethyl)-6 methoxynaphthalene are dissolved in 300 ml of methylene chloride and the solution is cooled using an ice bath. 6.0 ml (0.061 mol) of isopropyl isocyanate are added dropwise, whilst stirring. The reaction mixture is allowed to return to ambient temperature and left to stand overnight. The solution is then washed several times with water dried over $Na_2SO_4$ and evaporated. The residue is crystallised from ether. Melting point=128°-9° C.

The hydrochloride of the compound is prepared by adding hydrogen chloride in ether to a solution of the base in ethanol. The precipitate obtained is recrystallised from ethanol Melting point=234°-5° C.

The activity of the compounds has been demonstrated by their inhibition of the ADP-induced thrombus formation in the microvasculature of the hamster cheek pouch. This test is a modification of the technique originally described by:

1. Dulling, B. R., Berne, R. M. and Born, G. V. R. (1968) Microvas. Res., 1, 158.
2. Begent, N. and Born, G. V. R. (1970) Nature, 227, 926.
3. Begent, N. and Born. G. V. R. (1971) Brit. J. Pharmacol. 43, 580.

Male golden hamsters (*Mesocricetus auratus*), obtained from Wright's of Essex were housed in pairs in polypropylene cages. Their diet consisted of Spratt's Rodent Diet No. 1 and water ad libitum. One week's stabilization period was allowed before the commencement of dosing, the holding room being maintained at a constant temperature of 20° C.±2° C. and alternating light and dark periods of 12 h each.

All animals are dosed by gavage, 0.5 ml of the test solution being administered 2 h prior to the commencement of thrombus stimulation. This amount was varied slightly according to the weight of the animal.

The inhibitory effect of each drug on ADP-induced thrombus formation in the microvasculature of the hamster cheek pouch was assessed at 2 h after administering per os. The thrombus growth rate was determined at 5 min intervals over a period from 120 min to 180 min after dosing. The percentage of inhibition was calculated by comparison with results obtained in control animals at each time interval and the maximum degree of inhibition noted. The mean % inhibition for the complete experimental time period was also calculated.

When the administered dose is 50 mg/kg the percentage of inhibition is about 60%.

These results show that the compounds (I) are antithrombotic agents which may be used for the treatment of prophylaxis of thrombosis or occlusive vascular disease.

The compounds (I) may be advantageously combined with a compatible carrier so that they can be administered orally or parenterally. For oral administration any conventional pharmaceutical form may be used, that is to say tablets, dragees, gelatine-coated pills, capsules, cachets and drinkable solutions or suspensions.

The daily dose of the compound (I) is from about 200 mg to about 4000 mg.

We claim:

1. A method of treating or inhibiting thrombus formation or growth rate in a patient susceptible to thrombosis which comprises administering to a patient in need thereof an effective dosage to provide an antithrombotic effect of a compound having the formula

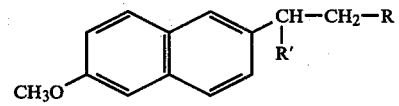

wherein
R' is H or $CH_3$
R is a

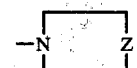

radical in which Z is O, S, SO, $SO_2$ or $NR_1$, $R_1$ being H, $C_6H_5$, $CH_3$, $CONR_2R_3$, $COOR_2$, $COR_2$ or $SO_2R_2$, where $R_2$ and $R_3$ are, independently, H, $C_{1-4}$ alkyl, $C_6H_5$ or $CF_3$.

2. A method of claim 1, wherein said compound (I) is 2-[2-(4-isopropylaminocarbonylpiperazino)-1-methylethyl]-6methoxynaphthalene or its hydrochloride.

* * * * *